United States Patent [19]

Klutchko

[11] 4,196,128

[45] Apr. 1, 1980

[54] PROCESS FOR THE PREPARATION OF 3-CYANOCHROMONES

[75] Inventor: Sylvester Klutchko, Ann Arbor, Mich.

[73] Assignee: Warner-Lambert Company, Morris Plains, N.J.

[21] Appl. No.: 969,117

[22] Filed: Dec. 13, 1978

[51] Int. Cl.² .......................................... C07D 311/22
[52] U.S. Cl. ................................................. 260/345.2
[58] Field of Search .......................... 260/345.2, 345.5

[56] References Cited

U.S. PATENT DOCUMENTS

| | | | |
|---|---|---|---|
| 3,825,574 | 7/1974 | Brown | 260/345.2 |
| 3,849,446 | 11/1974 | Strandtmann et al. | 260/345.2 |
| 3,853,921 | 12/1974 | Klutchko et al. | 260/345.2 |
| 3,862,143 | 1/1975 | Klutchko et al. | 260/345.2 |
| 3,879,411 | 4/1975 | Cairns et al. | 260/345.2 |
| 4,116,971 | 9/1978 | Strandtmann et al. | 260/308 D |

OTHER PUBLICATIONS

Ellis et al., Prog. Med. Chem. 9, pp. 93–94 (1973).

Ellis et al., J. Med. Chem., 15, 865 (1972).
Ellis, "Chromenes, Chromanones and Chromones," John Wiley & Sons (New York), p. 905.

*Primary Examiner*—Nicky Chan
*Attorney, Agent, or Firm*—George M. Kaplan; Albert H. Graddis

[57] ABSTRACT

3-cyanochromones having the following structural formula I:

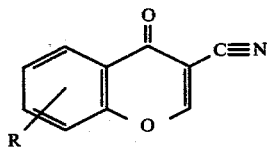

wherein R represents hydrogen, halogen or lower alkoxy, are prepared by dehydrating chromone-3-carboxamides with thionyl chloride in N,N-dimethylformamide. The compound having formula I is useful as an anti-allergic and anti-secretory agent.

4 Claims, No Drawings

PROCESS FOR THE PREPARATION OF 3-CYANOCHROMONES

The present invention relates to novel chromone derivatives and, more particularly, the present invention relates to the preparation of novel 3-cyanochromones having the following structural formula I:

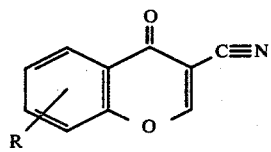

wherein R is hydrogen, halogen, lower alkoxy. In the above definition for R, the alkyl portion of alkoxy is meant to include lower aliphatic hydrocarbons having from one to seven carbon atoms in the carbon chain, preferably those having one to four carbon atoms such as methyl, ethyl, propyl, isopropyl, butyl or isobutyl.

The compounds prepared by the process of this invention, which form the basis for U.S. Pat. No. 3,862,143 to Klutchko, et al., issued Jan. 21, 1975, exhibit anti-allergy activity. Thus, for example, when they are tested in accordance with the procedure described by I. Mota, Life Sciences, 7, 465 (1963) and Z. Ovary and O. Bier, Proc. Soc. Exptl. Biol. Med., 81, 584 (1952), they are active at a dose of 5 mg to 100 mg/kg administered parenterally or orally to mammals such as rats or guinea pigs. They are indicated in allergic manifestations such as allergic bronchitis or intrinsic asthma.

In use, the compounds prepared by the process of this invention may be combined with a parenterally acceptable vehicle such as a gum tragacanth saline suspension, to provide dosage forms suitable for parenteral administration; or they may be combined with pharmaceutical diluents such as lactose, cornstarch, microcrystalline cellulose, Polyethylene Glycol 4,000 and/or 6,000, and the like, and formulated into tablet or capsule dosage form.

Generally speaking, to treat human beings, a dose of 20–50 mg orally, or by inhalation in the form of an aerosol spray, is prescribed to give symptomatic relief of asthma. The therapeutic spectrum of these compounds may be broadened by combining them with sympathomimetic agents such as isoproterenol or with steroids such as cortisone and its derivatives.

In addition to the above pharmacological activity, the compounds prepared by the process of this invention also exhibit anti-secretory effects and gastric anti-ulcer activity in experimental animals such as rats. For example, when they are tested according to the procedure according to H. Shay et al., Gastroenterology: 5,43 (1945), in the pylorus ligated rat they exhibit an ED of 20 mg to 50 mg/kg per body weight.

Further, the compounds prepared by the process of this invention are useful as intermediates for the production of other chromone derivatives. For example, compounds prepared by the process of this invention may be refluxed in the presence of tetrahydrofuran with aluminum chloride and sodium azide, to give compounds having the following formula:

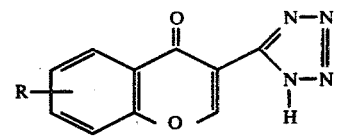

where R is hydrogen, halogen, lower alkoxy (lower alkoxy having the aforementioned meaning).

Compound II forms the basis of U.S. Pat. No. 4,116,971 to von Strandtmann et al., issued September 26, 1978.

U.S. Pat. No. 3,853,921 to Klutchko et al., issued Dec. 10, 1974 discloses preparation of these novel 3-cyanochromones by heating 3-formylchromones in formic acid in the presence of hydroxylamine. U.S. Pat. No. 3,862,143 also discloses preparation by this method in addition to preparation of 7-hydroxy, 7-alkoxy, or 7-acyloxy-3-cyanochromones by treating an appropriately substituted orthohydroxybenzoyl acetonitrile with an acid anhydride or acyl chloride. This latter method of preparation is also disclosed in U.S. Pat. No. 3,825,574 to Brown, issued July 23, 1974. Ellis, G. P., *Chromonenes Chromanones and Chromones,* John Wiley & Sons (New York) at page 905, discloses dehydration of 4-oxo-4H-1-benzopyran-2-carboxamide with thionyl chloride among other reagents, but states that this particular chromone-2-carboxamide is either unaffected by these reagents or gives a very low yield of corresponding nitrile. The same observation is reiterated in Ellis and Shaw, *J. Med. Chem.* 15: 865 (1972).

The present invention concerns a novel method of preparing these 3-cyanochromones from chromone-3-carboxylic acids. The reaction mechanism of the present invention may best be described by the following reaction scheme:

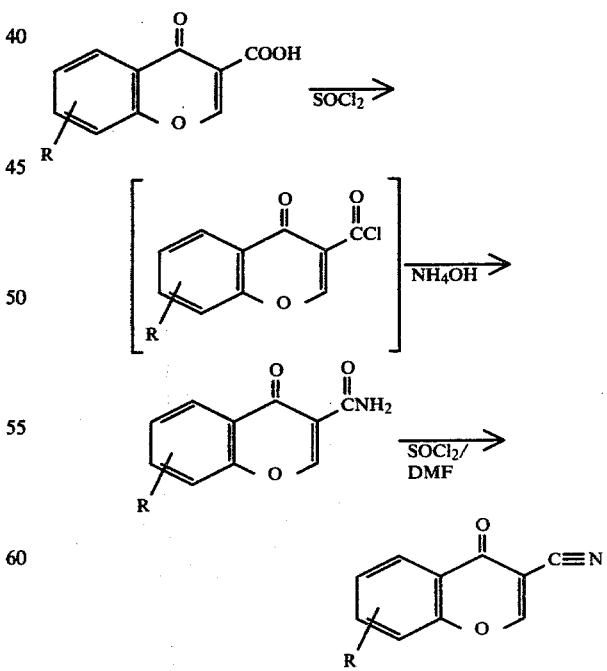

Referring to the reaction scheme, chromone-3-carboxylic acid is initially converted to the acyl chloride by treating with thionyl chloride as disclosed in U.S. Pat.

No. 3,849,446 to Von Strandtmann, et al., issued Nov. 19, 1974. The acyl chloride is then converted to the corresponding chromone-3-carboxamide, as disclosed in U.S. Pat. No. 3,862,143. The critical feature of the present invention is the further dehydration of the chromone-3-carboxamide with thionyl chloride in N,N-dimethylformamide to give the desired 3-cyanochromone in a high yield of at least 75%. Generally, a molar excess of thionyl chloride and a 30–40 molar excess of N,N-dimethylformamide are employed.

In order to further illustrate the practice of this invention, the following examples are included.

EXAMPLE I

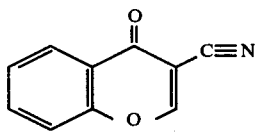

3-Cyanochromone

A quantity of 1.9 g (0.01 mole) of chromone-3-carboxamide (U.S. Pat. No. 3,862,143) was suspended in 20 ml of N,N-dimethylformamide. The mixture was cooled to 10° C. With stirring and ice bath cooling a quantity of 2.4 g (0.02 mole) of thionyl chloride was added over one minute. The ice bath was removed and the reaction mixture was allowed to warm to room temperature. All solid went into solution. After 5 minutes the solution was poured into 100 ml of ice water and the separated solid was filtered, washed well with water and dried; wt. 1.3 g (76%); mp. 170°–172° C. Recrystallization from ethyl acetate gave pure nitrile; mp 174°–176° C.

Anal. Calcd for $C_{10}H_5NO_2$; C, 70.18; H, 2.94; N, 8.18; Found: C, 70.18 H, 3.05; N, 8.22.

EXAMPLE II

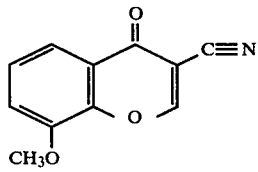

3-Cyano-8-methoxychromone

A quantity of 10.0 g (0.046 mole) of 8-methoxychromone-3-carboxylic acid, mp. 241°–243° C., (prepared as in U.S. Pat. No. 3,849,446), was added to 80 ml of thionyl chloride. The mixture was warmed to the boiling point. All solid went into solution. After 5 minutes at reflux most of the excess thionyl chloride was distilled off at reduced pressure. Chloro form (60 ml) was added and removed likewise. The solid acid chloride residue was dissolved in 40 ml of methylene Chloride. This solution was added gradually over 10 minutes to 100 ml of cold concentrated ammonium hydroxide with vigorous stirring and ice bath cooling. Ice water (100 ml) and petroleum ether (100 ml) were added and the entire mixture was filtered, washed well with water and dried; wt 9.0 g (90%); mp. 218°–220° C., tlc; SiO$_2$, EtOAc, one spot Rf 0.5. Recrystallization from methanol-methylene chloride gave pure 8-methoxychromone-3-carboxamide; m.p. 219°–221° C.

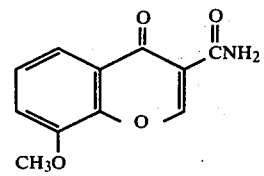

Anal. Calcd for $C_{11}H_9NO_4$: C, 60.27; H, 4.14; N, 6.39; Found: C, 59.87; H, 4.13; N, 6.35.

A quantity of 7.0 g (0.032 mole) of 8-methoxychromone-3-carboxamide was suspended in 80 ml of N,N-dimethylformamide. The mixture was cooled to 10° C. With stirring and good cooling a quantity of 7.6 g (0.064 mole) of thionyl chloride was added over 4 minutes, keeping the temperature at 10° C. After 5 minutes the ice bath was removed and the mixture was allowed to warm to room temperature. After 15 minutes the mixture was poured into 250 ml of ice water. The separated solid was filtered, washed well with water and dried; wt. 5.2 g (81%); mp 229°–231° C. Recrystallization from tetrahydrofuran gave pure nitrile; mp 232°–234° C.; tlc, SiO$_2$, EtOAc, one spot Rf 0.75.

Anal. Calcd for $C_{11}H_7NO_3$: C, 65.7, H, 3.51; N, 6.96. Found: C, 65.40; H, 3.56; N, 6.94.

I claim:
1. A process for preparing a compound of the formula

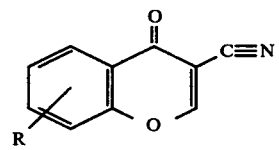

where R is hydrogen, lower alkyl, lower alkoxy; which comprises the steps of
(A) treating a compound of the formula

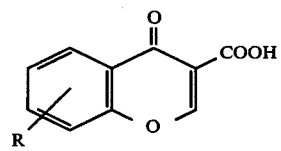

with thionyl chloride to
form a compound of the formula

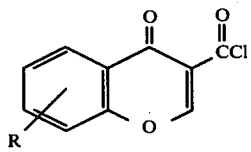

(B) treating this compound with ammonium hydroxide to form a compound of the formula

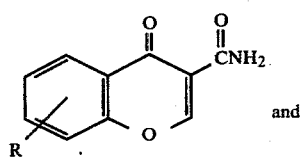

and (C) dehydrating this compound with thionyl chloride in N,N-dimethylformamide to obtain the final compound.

2. The process of claim 1 where 3-cyano-8-methoxychromone is prepared from 8-methoxychromone-3-carboxylic acid.

3. A process for preparing a compound of the formula

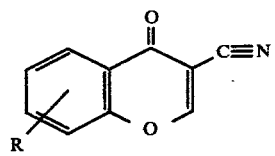

where R is hydrogen, lower alkyl, lower alkoxy; which comprises dehydrating a compound of the formula with thionyl chloride in N,N-dimethylformamide to obtain the final compound.

4. The process of claim 3 where 3-cyano-8-methoxychromone is prepared by dehydrating 8-methoxychromone-3-carboxamide.